United States Patent [19]

Beiter

[11] Patent Number: 4,545,376

[45] Date of Patent: Oct. 8, 1985

[54] BLOOD LANCET

[76] Inventor: Werner Beiter, Daimlerstrabe 8, 7735 Dauchingen, Fed. Rep. of Germany

[21] Appl. No.: 472,669

[22] Filed: Mar. 7, 1983

[30] Foreign Application Priority Data

Mar. 9, 1982 [DE] Fed. Rep. of Germany ....... 3208391

[51] Int. Cl.⁴ .............................................. A61B 5/14
[52] U.S. Cl. .................................................. 128/314
[58] Field of Search .......... 128/304, 314, 315, 329 R, 128/743, 744, 757, 770; 30/366; 206/367

[56] References Cited

U.S. PATENT DOCUMENTS

| 790,234 | 5/1905 | Waldo | 128/314 |
| 1,020,753 | 3/1912 | Ford | 128/314 |
| 3,086,647 | 4/1963 | Krezanoski | 206/634 X |
| 3,358,689 | 12/1967 | Higgins | 128/329 R |

FOREIGN PATENT DOCUMENTS

| A0017999 | 4/1980 | European Pat. Off. . | |
| 0017999 | 10/1980 | European Pat. Off. | 128/314 |
| A0061102 | 9/1982 | European Pat. Off. . | |
| A2130438 | 12/1972 | Fed. Rep. of Germany . | |
| A2909349 | 9/1980 | Fed. Rep. of Germany . | |
| A2150994 | 4/1973 | France . | |
| A975050 | 10/1963 | United Kingdom . | |
| 197861 | 6/1967 | U.S.S.R. | 128/329 |

Primary Examiner—Edward M. Coven
Attorney, Agent, or Firm—Lackenbach Siegel Marzullo Presta & Aronson

[57] ABSTRACT

In a blood lancet consisting of a handle and a tip, which are injection molded in one piece of plastic, there is provided according to the invention a protective yoke which protects the tip against damage. The protective yoke (24) is integrally molded to the handle in one piece, leaving predetermined break points, so that it can be broken off. The tip of rhombic cross-section comprises a base which imparts mechanical stability and limits the pricking depth, and an offset fine pricking tip.

10 Claims, 5 Drawing Figures

U.S. Patent
Oct. 8, 1985
4,545,376
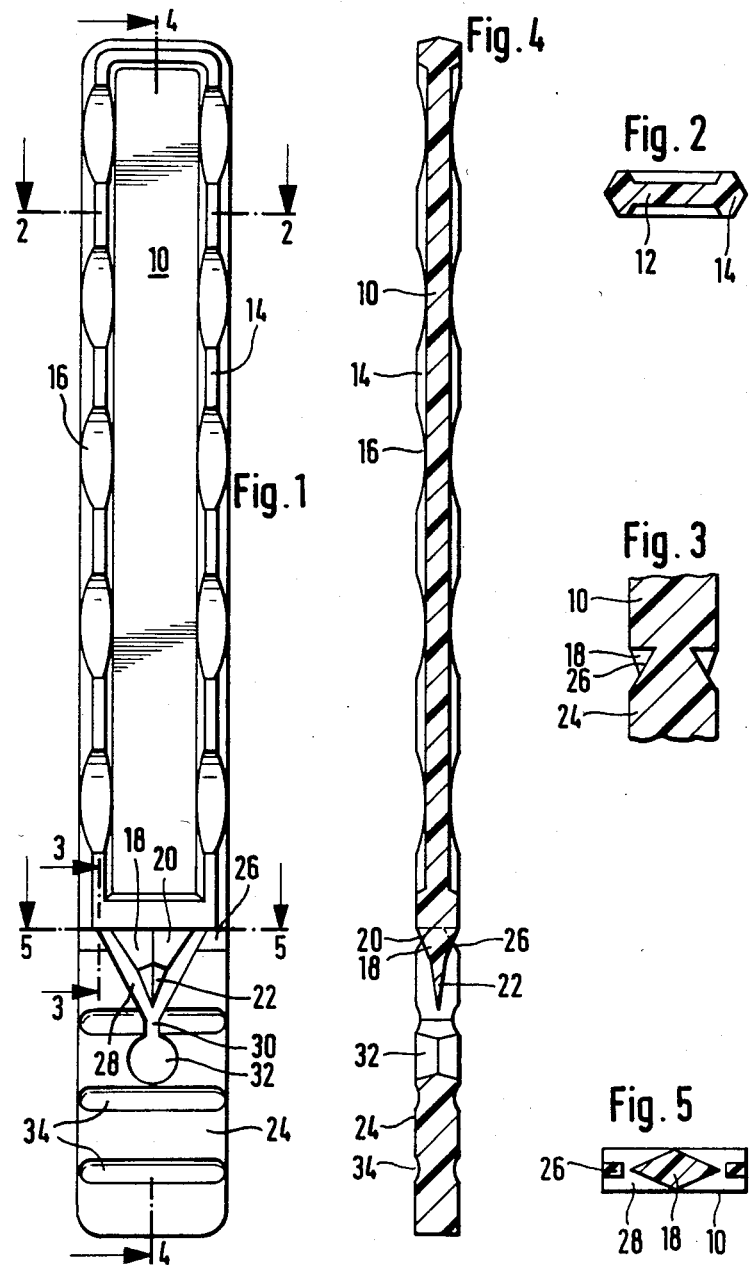

BLOOD LANCET

The invention relates to a blood lancet with a handle and a tip which are of plastic and is made in one piece.

Blood lancets are used for drawing a small amount of blood, e.g. for diagnostic purposes, by a short prick, preferably into the ball of the finger. As a rule one uses disposable lancets, to avoid the danger of infection. Common are blood lancets which are stamped out of a thin metal sheet. As precision machining of the tip is not possible for reasons of cost, the prick with such a blood lancet is relatively painful and leads to some subsequent bleeding of the prick wound.

Known also are blood lancets of the above mentioned kind which consist of a handle injection-molded of plastic in one piece with an integrally formed tip. The tip of these blood lancets is relatively blunt, because, on the one hand, a fine tip is difficult to produce by injection molding and, on the other, a fine tip easily breaks off during transport and storage. Because of the blunt tip, these known plastic blood lancets, too, create a painful and bleeding prick wound.

For use in connection with a device according to DE-OS No. 30 11 211 there is known lastly a blood lancet which consists of a fine steel needle which for retention in this device is cladded with plastic. To protect the fine tip, the tip is surrounded by a plastic protective cap, which is extruded in one piece with the retention and is twisted off before use of the lancet. Production of the fine steel needle and cladding it with plastic make this blood lancet very expensive.

It is the object of the invention to provide an inexpensive blood lancet which permits a prick as painless as possible and that does not continue to bleed.

In a blood lancet of the above mentioned kind, this problem is solved according to the invention in that a flat protective yoke is provided which is integrally formed in one piece on the handle to either side of the tip, and in that the tip is received in a recess which traverses the protective yoke normal to the surface extent thereof.

Preferably the two points of attachment of the protective yoke on the handle are formed as predetermined break points.

Preferably the tip has a cross-section which is elongated in one of its transverse axes and which widens toward the center of the cross-section in the direction of the other transverse axis perpendicular to the former. In particular, the tip has a rhombic cross-section and sharp lateral edges.

Expediently the tip may have a base of large pyramidal angle and an offset pricking tip of small pyramidal angle. The handle and protective yoke may have essentially the same flat cross-section, their thickness corresponding to the minor diagonal of the rhombic base area of the tip.

Preferably the distance between the tip and protective yoke is smaller than the thickness of the yoke.

Preferably the recess is prolonged axially contiguous to the tip in a slit which opens into a vent hole that traverses the protective yoke.

The handle and protective yoke may have grip depressions.

Expediently the handle has a thin central zone and a thicker peripheral edge, the grip depressions being formed, if desired, in this peripheral edge.

The blood lancet according to the invention is entirely of plastic and is made in one piece by injection molding. Because of the flat form of the blood lancet as a whole, little material is required, so that it can be produced very inexpensively.

The protective yoke around the tip prevents damage to the tip during transport and storage, so that the tip may be made very fine, with the result of a fine prick which involves little pain and causes no bleeding wound.

Preferably the tip is offset. It has a wide base, the pyramidal angle of which is large, that is, obtuse, and a fine pricking tip which is sharply pointed, that is, has a small pyramidal angle. The actual prick is made only with the fine pricking tip, while the broader base of this tip provides the necessary mechanical strength and limits the pricking depth. This makes possible a fine prick involving little pain and causing no secondary bleeding.

As to injection molding technique, the formation of the fine tip is facilitated especially by the fact that the yoke recess receiving the tip communicates through a slit, with a vent hole in the region of the tip. Thus the mold can be vented directly at the fine tip, so that the plastic material flows into the fine tip neatly and completely.

The protective yoke is formed flat and surrounds the tip only along the peripheral line thereof. It is therefore very easy to break the yoke off by bending it perpendicular to its surface extent, to make the blood lancet ready for use. The breaking off of the yoke is further facilitated by the fact that its points of attachment on the handle are formed as predetermined break points where the material is thin.

Although the protective yoke surrounds the tip only along the circumference thereof, complete and reliable protection of the tip against damage is ensured by the fact that the distance between the tip's circumferential edge and the yoke is smaller than the thickness of the yoke. In this manner the yoke sufficiently covers the especially sensitive regions of the tip also perpendicular to its surface extent, namely the pricking tip and the sharp lateral edges of the cross-sectionally rhombic tip which make the incision.

In the following, the invention will be explained more specifically with reference to an embodiment illustrated in the drawing, in which:

FIG. 1 shows a top view of a blood lancet of the invention;

FIG. 2, a section along line 2—2 of FIG. 1;

FIG. 3, a section along line 3—3 of FIG. 1;

FIG. 4, a section along line 4—4 of FIG. 1; and

FIG. 5 a section along line 5—5 of FIG. 1.

The blood lancet, shown greatly enlarged in the drawing, is made of plastic in one piece by injection molding.

The blood lancet comprises a handle 10 of flat cross-section, as shown in FIG. 2. In the central region 12, the handle 10 is thin, while its peripheral edge 14 is thicker. This results in a low requirement of material, combined with high mechanical strength and rigidity. In the thickened circumferential edge 14 grip depressions 16 are formed, which ensure reliable gripping and holding of the lancet.

At the front end face of handle 10 a tip 18 is integrally formed in one piece. As FIG. 5 shows, the tip 18 has the cross-sectional form of a flat, elongated rhombus. The tip 18 adjoins the handle 10 with a wide base 20 which comes to a blunt point with a relatively large conical angle. Contiguous to the base 20 and offset is the actual pricking tip 22, which comes to a sharp point with a smaller conical angle.

As FIG. 5 shows, the shorter diagonal of the base area of tip 18 corresponds to the thickness of the peripheral edge 14 of the handle 10, so that an optimum mechanical stability of the tip is obtained. In the widthwise extent of handle 10 the rhombic cross-section of the tip 18 extends longitudinally, so that acute-angle cutting edges of the tip 18 result. The front end face of handle 10 has further integrally formed on it in one piece a protective yoke 24. The protective yoke 24 attaches on either side of the tip 18 at the edge of handle 10. At the points of attachment the thickness of the yoke is reduced, so that predetermined break points 26 result.

In the region of tip 18, the protective yoke 24 has a recess 28 which extends through perpendicularly to its surface extent and which, as FIG. 1 shows, corresponds in its form to the projection of tip 18 into the plane of handle 10. The dimensions of the recess 18 are chosen so that the distance of the cutting edges of tip 18 from yoke 24, i.e. from the edge of recess 28, is smaller than the thickness of yoke 24.

At its front, pointed end, recess 28 ends in an axial slit 30, which in turn opens into a vent hole 32 traversing yoke 24. Through slit 30 and vent hole 32 the injection mold can be vented during the molding of the fine pricking tip 22.

The protective yoke 24 also has grip depressions 34 before the tip 18. To make the blood lancet ready for use, the protective yoke is seized in the area before the tip 18, this being facilitated by the grip depressions 34, and is broken off along the predetermined break points 26 by bending out of the plane of the drawing of FIG. 1.

I claim:

1. A relatively flat blood lancet, having a handle portion and a tip portion having sharp edges, which portions are made of plastic in one piece, comprising:
a flat protective yoke-like guard integrally formed as a part of said one piece of plastic, and said protective yoke-like guard being attached at two weakened breakoff points to said handle only on opposite sides of said tip but free of any contact therewith, with said tip being received unobstructedly in a cutout-like recess form transversely of said protective yoke-like guard; and said tip being spaced away so as to be free from said protective yoke-like guard, thereby leaving the sharp edges of said tip free and clear of any plastic material, and said two weakened breakoff attachment points of said protective yoke-like guard adapted to be broken off by bending said protective yoke-like guard in a direction perpendicular to a plane passing through said blood lancet.

2. The blood lancet according to claim 1, wherein the two weakened breakoff attachment points of the said protective yoke-like guard on the opposite sides of said tip are formed as predetermined break points.

3. The blood lancet according to claim 1, wherein said tip has a cross-section which is elongated in one of its transverse axis and which widens toward the center of the cross-section in the direction of the other transverse axis normal to the former.

4. The blood lancet according to claim 3, wherein said tip is rhombic in cross-section and has sharp lateral side edges.

5. The blood lancet according to claim 3, wherein said tip has a base of large pyramidal angle and an offset pricking tip of a smaller pyramidal angle.

6. The blood lancet according to claims 3 or 5, wherein said handle and said protective yoke-like guard have essentially the same flat cross-section, and their thickness corresponds to the minor diagonal of the rhombic base area of said tip.

7. The blood lancet according to claim 6, wherein the distance between said tip and said protective yoke-like guard is smaller than the thickness of the protective yoke-like guard.

8. The blood lancet according to claim 7, wherein axially contiguous to said tip, said recess is lengthened by means of a longitudinal slit which opens into a vent hole formed transversely of said protective yoke-like guard.

9. The blood lancet according to claim 7, wherein said handle and said protective yoke-like guard are provided with a plurality of gripping depressions.

10. The blood lancet according to claim 7, wherein said handle has a thin central region and a thicker peripheral edge, and said gripping depressions of said handle are formed in said peripheral edge.

* * * * *